United States Patent [19]

Scheer

[11] Patent Number: 6,080,746
[45] Date of Patent: Jun. 27, 2000

[54] METHODS AND COMPOSITIONS FOR THE PROPHYLAXIS AND TREATMENT OF CYTOMEGALOVIRUS INFECTIONS

[76] Inventor: David I. Scheer, Scheer & Company, Inc., 250 W. Main St., Branford, Conn. 06405

[21] Appl. No.: 07/776,895

[22] Filed: Oct. 16, 1991

Related U.S. Application Data

[63] Continuation of application No. 07/489,458, Mar. 6, 1990, abandoned.

[51] Int. Cl.$^7$ ............................ A61K 7/16; A61K 7/035; A61K 7/42
[52] U.S. Cl. ............................ 514/258; 514/261; 514/262
[58] Field of Search .................................. 514/25 F, 261, 514/262

[56] References Cited

U.S. PATENT DOCUMENTS

| | | | |
|---|---|---|---|
| 4,177,348 | 12/1979 | Shealy et al. | 544/312 |
| 4,232,154 | 11/1980 | Shealy et al. | 544/250 |
| 4,396,623 | 8/1983 | Shealy et al. | 424/257 |
| 4,543,255 | 9/1985 | Shealy et al. | 514/258 |
| 4,728,736 | 3/1988 | Shealy et al. | 544/254 |
| 4,857,531 | 8/1989 | Borthwick et al. | 514/262 |
| 4,916,224 | 4/1990 | Vince et al. | 544/234 |
| 4,931,559 | 6/1990 | Vince et al. | 544/276 |
| 4,950,758 | 8/1990 | Vince et al. | 544/276 |

FOREIGN PATENT DOCUMENTS

| | | |
|---|---|---|
| 219 838 | 4/1987 | European Pat. Off. . |
| 236 935 | 9/1987 | European Pat. Off. . |

OTHER PUBLICATIONS

*Am. J. Opthalmol.,* Rosecan et al, vol. 101 pp. 405–418 (1986).

*Antiviral Research,* De Clercq et al, "Broad Spectrum Antiviral Activity of the Carbocyclic Analog of 3–Deazaadenosine", vol. 3, pp. 17–24 (1983) and vol. 4, pp. 119–133 (1984).

*Journal of Medicinal Chemistry,* Shealy et al, "Synthesis & Antiviral Evaluation of Carbocyclic Analogues of Ribofuranosides of 2–Amino–6–Substituted–purines and 2–Amino–6–Substituted 8–Azapurines", vol. 27, pp. 670–674 (1984).

*Journal of Pharmaceutical Sciences,* Shealy et al, vol. 62, pp. 1432–1434 (1973).

*Journal of Medicinal Chemistry,* Shealy et al., "Synthesis and Antiviral Activity of Carbocyclic Analogues of 2'–Deoxyribofuranosides of 2–Amino–6–substituted–purines and of 2–Amino–6–substituted–8–Azapurines", vol. 27, pp. 1416–1421 (1984).

*Journal of Medicinal Chemistry,* Shealy et al., "Synthesis and Antiviral Evaluation of Carbocyclic Analogues of 2–Amino–6–substituted–purine 3'–Deoxyribofuranosides", vol. 30 pp. 1090–1094 (1987).

*Antiviral Research,* Vince et al., "Second International Conference on Antiviral Research, Williamsburg, Va., 1988" vol. 9 p. 120 (1988).

*Journal of Heterocyclic Chemistry,* Shealy et al., "Synthesis of the Carbo–cyclic Analogs of Uracil Nucleosides", vol. 13 pp. 1015–1020 (1976).

*Journal of Heterocyclic Chemistry,* Shealy et al., "Acid Catalyzed Cyclization of Alkoxyacryloylureas to 2.4 (1H, 3H) pyrimidinediones", vol. 13, pp. 1041–1047 (1976).

*Journal of Medicinal Chemistry,* Shealy et al., "Carbocyclic Analgoues of S–Substituted Uracil Nucleoside: Synthesis and Antiviral Activity", vol. 26 pp. 156–165 (1983).

*Journal of Heterocyclic Chemistry,* Shealy et al., "The Carbocyclic Analog of Cytidine, Synthesis and Anti–neoplastic Activity", vol. 13, pp. 1353–1354 (1976).

*Journal of Heterocyclic Chemistry,* Shealy et al., vol. 17 pp. 353–358 (1980).

*Journal of Heterocyclic Chemistry,* Shealy, et al., "Carbocyclic Analogs of Thymines Nucleosides & Related I–Substituted Thymines", vol. 18, pp. 383–389 (1981).

Buthala et al., Annals N.Y. Acad. Sciences vol. 130, 17–23 (1965).

Machida, Antimicrob. Agents and Chemotherapy, vol. 29, 524–526 (1986).

DeClercq, Verh. K. Acad., Geneeskd. Belg. 50, 261–290 (1988).

Abstract of EP 236 935 A.

Abstract of EP 219 838 A.

Abstract of JP 233 146.

Biggadike et al., J. Chem. Soc. Commun., 1083–4 (1987).

Fields, Virology, 1985, Raven Press pp. 630–631.

Microbiology, 2nd Ed, Davis et al, Hoper & Rowe 1973 p. 1239.

Secrist et al., Resolution of Racemi Carbocyclic Analogues of Purine Nucleosides through the Action of Adenosine Deaminase. Antiviral Activity of the Carbocyclic 2'–Deoxyguanosine Enantiomers, J. Med. Chem. 30:746–749 (1987).

*Primary Examiner*—Russell Travers
*Attorney, Agent, or Firm*—Fish & Richardson P.C.

[57] ABSTRACT

Methods and compositions for preventing or treating cytomegalovirus infections by the use of carbocyclic analogues of purine and pyrimidine nucleosides.

1 Claim, No Drawings

METHODS AND COMPOSITIONS FOR THE PROPHYLAXIS AND TREATMENT OF CYTOMEGALOVIRUS INFECTIONS

This application is a continuation of application Ser. No. 07/489,458, filed Mar. 6, 1990, now abandoned.

TECHNICAL FIELD OF THE INVENTION

This invention relates to the prophylaxis and treatment of cytomegalovirus (CMV) infections in mammals, and relates more particularly to the use of carbocyclic analogues of purine and pyrimidine nucleosides in the prophylaxis and treatment of cytomegalovirus infections.

Cytomegalovirus infections have been observed in numerous patients (including neonates) suffering from suppression of cell-mediated immunity, either as a result of immunosuppression (as in the case of organ transplant recipients) or acquired immune deficiency syndrome. Chief among such infections are those within the eye caused by cytomegalovirus (CMV) such as chorioretinitis, although infections of other organs, such as hepatitis, esophagitis, gastritis, pneumonitis, or encephalitis caused by this virus have also been observed.

Although a number of antiviral agents are well known, such as acyclovir, alpha-interferon, and vidarabine, and although acyclovir, at least, is widely recommended and used for treatment of disseminated herpes simplex virus infections, it has been reported by Rosecan et al., Am. J. Opthalmol. Vol. 101, 405–418 (1986) that attempts at treating cytomegalovirus retinitis with these antiviral agents have been unsuccessful. Broad spectrum antibiotics, corticosteroids, and antifungal agents have also been reported to be without therapeutic benefit against this disease. An antiviral agent, ganciclovir (dihydroxy propoxymethyl guanine) (DHPG) an acyclic nucleoside, has been reported to be effective against CMV retinitis but is of limited potency and is associated with dose-limiting toxicity. Its activity is described in Declercq et al, Antiviral Research Vol. 3, 17–24 (1983) and Vol. 4, 119–133 (1984).

In general, although acyclovir has been used as prophylaxis against CMV infections, it has been reported to be ineffective against established systemic CMV infections as well as against CMV retinitis.

SUMMARY OF THE INVENTION

This invention relates to compositions and methods for the prevention and treatment of CMV infections, in mammals including man, characterized by an antivirally effective amount of a compound selected from the group consisting of formulae:

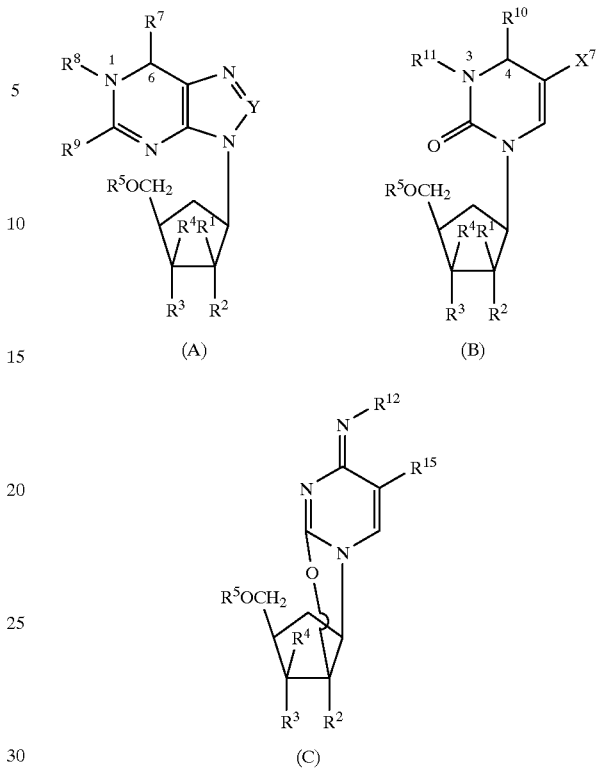

wherein:
$R^1$ and $R^4$ are independently either hydrogen, hydroxyl, acyloxy or together form a bond;
$R^2$ is selected from the group consisting of hydrogen, acyloxy and hydroxyl;
$R^3$ is selected from the group consisting of hydrogen, hydroxyl, acyloxy and $OR^6$;
$R^5$ is selected from the group consisting of hydrogen, a $C_{1-6}$ alkanoyl group and an aroyl group;
$R^6$ is selected from the group consisting of hydrogen, a $C_{1-6}$ alkanoyl group and an aroyl group;
$R^7$ is selected from the group consisting of oxygen and sulfur bound through a double bond to carbon 6 when $R^8$ is hydrogen; or selected from the group consisting of halogen, an amino group, an alkylthio group when $R^8$ is bound to carbon 6 to form a double bond between the nitrogen of position 1 and the carbon of position 6;
Y is selected from the group consisting of CH and nitrogen (N);
$R^9$ is selected from the group consisting of hydrogen and amino;
$R^{10}$ is selected from the group consisting of oxygen bound through a double bond to carbon 4 when $R^{11}$ is hydrogen; and $NR^{12}R^{13}$ when $R^{11}$ is bound to carbon 4 to form a double bond between the nitrogen of position 3 and the carbon of position 4;
$R^{12}$ and $R^{13}$ are independently hydrogen or a $C_{1-6}$ alkyl group;
$X^1$ is selected from the group consisting of hydrogen, halogen (including fluorine, chlorine, bromine or iodine), a $C_{1-6}$ alkyl group, and $NHR^{14}$ wherein $R^{14}$ is a $C_{1-6}$ alkyl group;
$R^{15}$ is selected from the group consisting of hydrogen, a $C_{1-6}$ alkyl group or halogen (including fluorine, chlorine, bromine or iodine).

DETAILED DESCRIPTION OF THE INVENTION

The present invention provides novel methods and compositions for the prophylaxis and treatment of infections caused by the cytomegalovirus, particularly intravitreal infections of the eye. The present invention particularly relates to the treatment and prophylaxis of CMV infections using methods and compositions characterized by certain carbocyclic analogues of nucleosides.

The term "carbocyclic analogue of a nucleoside" refers to compounds which possess a cyclopentane ring in place of the tetrahydrofuran ring of the analogous nucleoside. The substitution of cyclopentane for the tetrahydrofuran moiety is thought to increase the resistance of the carbocyclic analogues of nucleosides to the action of degradative enzymes and may also increase the selectivity of their biologic actions.

U.S. Pat. No. 4,396,623 (Shealy et al.) refers to the use of certain carbocylic analogs or uracil nucleosides for the treatment of various human and animal diseases caused by DNA viruses, such as Herpes simplex virus. U.S. Pat. Nos. 4,177,348 (Shealy et al.) and 4,232,154 (Shealy et al.) refer to carbocyclic analogues of cystosine nucleosides and their activity against DNA viruses, such as herpes simplex virus Type 1 and vaccina virus, and RNA viruses such as rhinovirus Type 1A and influenza virus. U.S. Pat. Nos. 4,543,255 (Shealy et al.) and 4,728,736 (Shealy et al.) refer to carbocyclic analogues of purine 2'-deoxyribofuranosides and ribofuranosides, respectively, and their activity against DNA viruses, exemplified by herpes simplex virus Type 1 and Type 2.

The methods and compositions of this invention are characterized by an antivirally effective amount of a compound of the formulae:

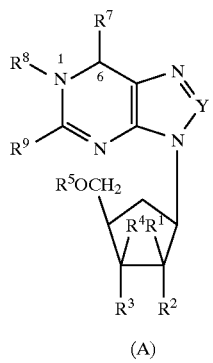

(A)

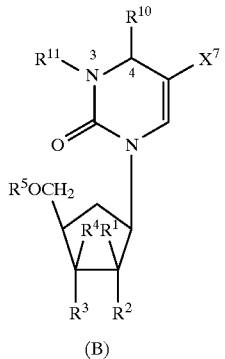

(B)

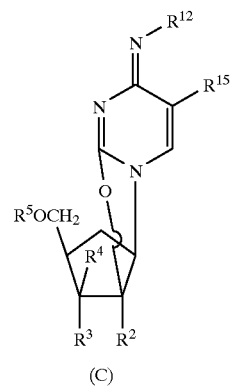

(C)

wherein:

$R^1$ and $R^4$ are independently either hydrogen, hydroxyl, acyloxy or together form a bond (when $R^1$ and $R^4$ together form a bond, a double bond is formed between the carbons of the cyclopentane ring to which $R^1$ and $R^4$ are attached in formulae A and B);

$R^2$ is selected from the group consisting of hydrogen, acyloxy and hydroxyl;

$R^3$ is selected from the group consisting of hydrogen, hydroxyl, acyloxy and $OR^6$;

$R^5$ is selected from the group consisting of hydrogen, a $C_{1-6}$ alkanoyl group and an aroyl group;

$R^6$ is selected from the group consisting of hydrogen, a $C_{1-6}$ alkanoyl group and an aroyl group;

$R^7$ is selected from the group consisting of oxygen and sulfur bound through a double bond to carbon 6 when $R^8$ is hydrogen; or selected from the group consisting of halogen, an amino group, an alkylthio group when $R^8$ is bound to carbon 6 to form a double bond between the nitrogen of position 1 and the carbon of position 6;

Y is selected from the group consisting of CH and nitrogen (N);

$R^9$ is selected from the group consisting of hydrogen and amino;

$R^{10}$ is selected from the group consisting of oxygen bound through a double bond to carbon 4 when $R^{11}$ is hydrogen; and $NR^{12}R^{13}$ when $R^{11}$ is bound to carbon 4 to form a double bond between the nitrogen of position 3 and the carbon of position 4;

$R^{12}$ and $R^{13}$ are independently hydrogen or a $C_{1-6}$ alkyl group;

$X^1$ is selected from the group consisting of hydrogen, halogen (including fluorine, chlorine, bromine or iodine), a $C_{1-6}$ alkyl group, and $NHR^{14}$ wherein $R^{14}$ is a $C_{1-6}$ alkyl group;

$R^{15}$ is selected from the group consisting of hydrogen, a $C_{1-6}$ alkyl group or halogen (including fluorine, chlorine, bromine or iodine).

The above-described compositions and methods in addition to being useful in treating or preventing CMV infections are surprisingly advantageous over presently available agents and methods. First, the carbocyclic analogues of this invention have not been observed to be significantly incorporated into host cell DNA. The methods and compositions of the present invention have high potency and are advantaged over prior methods and compositions which utilize compounds which are incorporated into host cell DNA and which may cause chromosomal damage. Furthermore, the methods and compositions of this invention are not plasma derived so they carry no risk of serum carried infections and infectious agents.

In the more preferred methods and compositions of this invention an antiviral effective amount of a compound of Formulae I–XI is employed, wherein Y is N or CH and X of Formulae I, III, V, VII, and IX is halogen, an amino group, an alkylamino group, an alkoxy group, or an alkylthio group, and X of Formulae II, IV, VI, VIII, X, and XI is oxygen or sulfur:

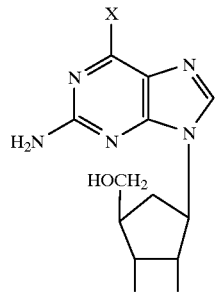

Formula I

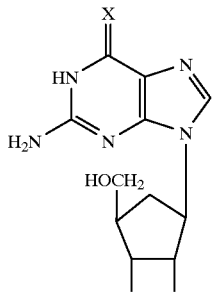

Formula II

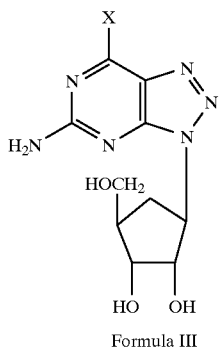

Formula III

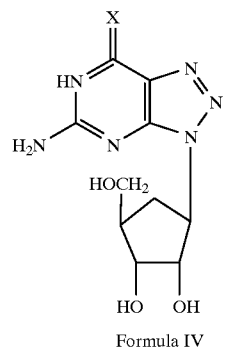

Formula IV

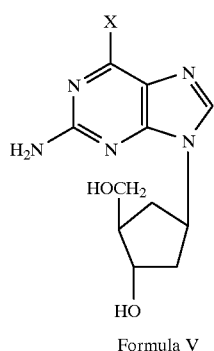

Formula V

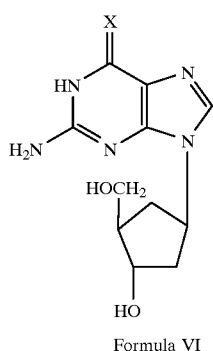

Formula VI

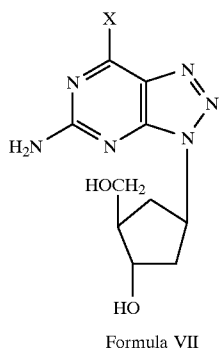

Formula VII

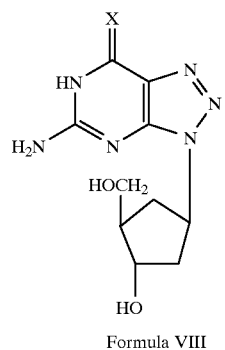

Formula VIII

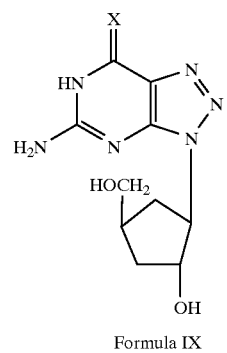

Formula IX

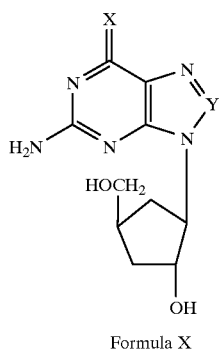

Formula X

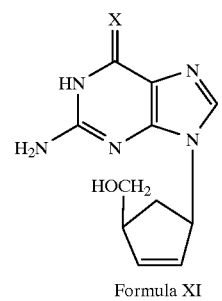

Formula XI

In all of the above structures for Formulae I–XI, X represents the $R^7$ moiety of structure A described supra.

The compounds represented by Formulae I–XI are carbocyclic analogues of various nucleosides:

Carbocyclic analogues of ribofuranosides of 2-amino-6-substituted-purines, Formulae I and II.

Carbocyclic analogues or ribofuranosides of 2-amino-6-substituted-8-azapurines, Formulae III and IV.

Carbocyclic analogues of 2'-deoxyribofuranosides of 2-amino-6-substituted-purines, Formulae V and VI.

Carbocyclic analogues of 2'-deoxyribofuranosides of 2-amino-6-substituted-8-azapurines, Formulae VII and VIII.

Carbocyclic analogues of 3'-deoxyribofuranosides of 2-amino-6-substituted-purines, Formulae IX and X with Y=CH.

Carbocyclic analogues of 3'-deoxyribofuranosides of 2-amino-6-substituted-8-azapurines, Formulae IX and X with Y=N.

Carbocyclic analogues of 2-amino-6-substituted purine 2', 3'-didehydro-2', 3'-dideoxy nucleosides represented by Formula XI.

Most preferably, the carbocyclic analogue useful in the methods and compositions of this invention is 2'-deoxyguanosine ("2'-CdG"), i.e., the compound of Formula VI where X—O.

Also greatly preferred are the prodrugs of 2'-CdG, that is, those drugs which are metabolized in vivo to 2'-CdG, such as those compounds having Formula A where $R^1$, $R^2$, and $R^4$ are hydrogen, $R^3$ and $R^5$ are independently hydroxyl or alkanoyl (preferably $C_{1-6}$ alkanoyl), $R^7$ is oxygen bound through a double bond to carbon 6 when $R^8$ is hydrogen, or $R^7$ is alkoxy (preferably $C_{1-6}$ alkoxy) when $R^8$ is bound to carbon 6 to form a double bond between the nitrogen of position 1 and the carbon of position 6, and $R^9$ is amino.

Preferably, in accordance with this invention, the above-described compounds are used against CMV infections and, more preferably, the above-described preferred compounds, and most preferably 2'-CDG, are used in methods and compositions of this invention against that infection.

The compounds used in the treatments of this invention can be synthesized from known and readily available materials by well known, conventional methods.

For example, synthesis of carbocyclic analogues of nucleosides represented by Formulae I–IV are described in the following publications.

Y. F. Shealy, J. D. Clayton, G. Arnett, and W. M. Shannon, "Synthesis and Antiviral Evaluation of Carbocyclic Analogues of Ribofuranosides of 2-Amino-6-substituted-purines and of 2-Amino-6-substituted-8-Azapurines", *Journal of Medicinal Chemistry*, Volume 27, pages 670–74 (1984).

Y. F. Shealy and J. D. Clayton, U.S. Pat. No. 4,728,736, Mar. 1, 1988.

Syntheses of the carbocyclic analogue of guanosine is described in Y. F. Shealy and J. D. Clayton, Journal of Pharmaceutical Sciences, Volume 62, pages 1432–34 (1973).

Synthesis of carbocyclic analogues of nucleosides represented by Formulae V–VIII are described in the following publications.

Y. F. Shealy, C. A. O'Dell, W. M. Shannon and G. Arnett, "Synthesis and Antiviral Activity of Carbocyclic Analogues of 2'-Deoxyribofuranosides of 2-Amino-6-substituted-purines and of 2-Amino-6-substituted-8-azapurines", *Journal of Medicinal Chemistry*, Volume 27, pages 1416–21 (1984).

Y. F. Shealy and C. A. O'Dell, U.S. Pat. No. 4,543,255, Sep. 24, 1985.

Syntheses of carbocyclic analogues of nucleosides represented by Formulae IX and X are described in the article by Y. F. Shealy, C. A. O'Dell, and G. Arnett, "Synthesis and Antiviral Evaluation of Carbocyclic Analogues of 2-Amino-6-substituted-purine 3'-Deoxyribofuranosides", *Journal of Medicinal Chemistry*, Volume 30, pages 1090–94 (1987).

The synthesis of the carbocyclic analogue of 2',3'-didehydro-2',3'-dideoxyguanosine (carbovir), was reported by R. Vince et al., "Second International Conference on Antiviral Research, Williamsburg, Va., 1988". Abstract, *Antiviral Research*, Volume 9, page 120 (1988).

Syntheses of carbocyclic analogs of uracil nucleosides are described in the following publications.

Y. F. Shealy, and C. A. O'Dell, "Synthesis of the Carbocyclic Analogs of Uracil Nucleosides", *Journal of Heterocyclic Chemistry*, Volume 13, pages 1015–20 (1976).

Y. F. Shealy, and C. A. O'Dell, "Acid-Catalyzed Cyclization of Alkoxyacryloylureas to 2,4(1H,3H) pyrimidinediones", *Journal of Heterocyclic Chemistry*, Volume 13, pages 1041–47 (1976).

Y. F. Shealy, C. A. O'Dell, W. M. Shannon, and G. Arnett, "Carbocyclic Analogues of 5-Substituted Uracil Nucleoside: Synthesis and Antiviral Activity", *J. Med. Chem.*, Volume 26, pages 156–65 (1983).

U.S. Pat. No. 4,396,623 (Y. F. Shealy, C. A. O'Dell and W. M. Shannon).

Syntheses of carbocyclic analogs of cytosine nucleosides are described in the following publications.

U.S. Pat. Nos. 4,177,348 and 4,232,154 (Y. F. Shealy and C. A. O'Dell);

Y. F. Shealy and C. A. O'Dell, "The Carbocyclic Analog of Cytidine, Synthesis and Anti-neoplastic Activity", *Journal of Heterocyclic Chem.*, Volume 13, pages 1353–54 (1976).

Y. F. Shealy and C. A. O'Dell, *J. of Heterocyclic Chem.*, Volume 17, pages 353–58 (1980).

Syntheses of carbocyclic analogs of thymine nucleosides are described in the following publication.

Y. F. Shealy, C. A. O'Dell, and M. C. Thorpe, "Carbocyclic Analogs of Thymine Nucleosides and Related I-Substituted Thymine", *J. Heterocyclic Chem.*, Volume 18, pages 383–89 (1981).

Depending on the route of administration, which could normally be either intravitreal injection, topical (in the case of localized infections such as CMV-induced keratoconjunctivitis), oral or parenteral, the compounds may be in the form of a solid, semi-solid, liquid, oil, ingestible capsule or liposome or microencapsulated dosage form and may either be present as the original compound or in the form of a pharmaceutically acceptable salt in association with or without an appropriate pharmaceutical carrier, including water and normal saline, among others.

The antivirally effective dose of the compounds to be used in accordance with this invention to provide prophylaxis and treatment can be determined by methods known in the art. While 100 µg/kg of 2'-CdG every 48 hours when injected intravitreally in water or normal saline for a week is well tolerated and antivirally effective, dosages as small as 10 µg/kg or as high as 10 mg/kg per day may be used depending upon the mode of administration and whether prophylaxis or treatment is desired. Effective dosages may be administered also in sustained release dosage form.

EXAMPLES

Racemic 2'-CdG(±2'-CdG) and the racemic carbocyclic analogue of 2,6-diaminopurine-2'-deoxyribofuranoside (±C-2,6'-DAPdR) having the structure of Formula V in which X is amino were prepared as described in Shealy et al U.S. Pat. No. 4,543,255 and evaluated for inhibition of human cytomegalovirus (strain AD 169) replicating in human diploid embryonic lung cells (MRC5) by a plaque reduction assay. Also evaluated under the same conditions were prior art drugs Ara-A and ganciclovir (DHPG). In each case, drug treatment began 0 hr. postinfection. The results are set forth in Table 1 below:

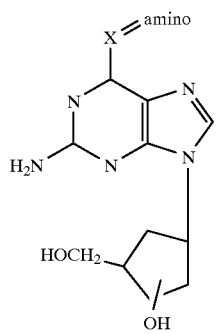

In addition, the racemic carbocyclic analogue of the 2,6-diaminopurine ribofuranoside (DAPR) was found to have $MIC_{50}$ of 8.7 μg/mL and a therapeutic index of 40 when tested under the same conditions, and the racemic carbocyclic analogue 2-amino-6-methoxypurine 2'-deoxyribofuranoside (AMPdR) exhibited $MIC_{50}$ of less than 0.9 μg/mL with a therapeutic index greater than 105, also when tested under the same conditions. The D-2'-deoxyguanosine-5'-0-valerate exhibited an $ED_{50}$ of 0.09 μg/ml and racemic 2'-deoxyguanosine-3',5'-0-diisobutyrate exhibited an $ED_{50}$ of 3.9 μg/ml, in a plaque reduction assay against human CMV.

Similar results were obtained upon evaluating mixtures of racemic 2'-CdG and DHPG, as shown in Table 2 below:

TABLE 1

|  | Reduction (%) of $CPE^1$ at Time of Harvest | Drug Cytotoxicity (gross morphology) | CMV Yield ($\log_{10} CCID_{50}$/ml)$^2$ |
|---|---|---|---|
| ±2$^1$-CdG |  |  |  |
| 32 μg/ml | — | toxic | — |
| 10 | 100 | sl. toxic | 0 |
| 3.2 | 100 | v. sl. toxic | 1.0 |
| 1.0 | 95 | 0 | 3.6 |
| 0.32 | 20 | 0 | 4.5 |
| 0.1 | 0 | 0 | 5.0 |
| 0.032 | 0 | 0 | 5.4 |
| 0 (Virus Control) |  |  | 5.5 |
| ±C-2$^1$6$^1$-DAPdR |  |  |  |
| 32 μg/ml | — | toxic | — |
| 10 | 100 | sl. toxic | 0 |
| 3.2 | 100 | v. sl. toxic | 0 |
| 1.0 | 95 | 0 | 3.4 |
| 0.32 | 25 | 0 | 4.0 |
| 0.1 | 0 | 0 | 5.0 |
| 0.032 | 0 | 0 | 5.3 |
| 0 (Virus Control) |  |  | 5.5 |
| Ara-A |  |  |  |
| 100 μg/ml | 100 | partial toxicity; CPE discernible | 0 |
| 32 | >95 | sl. toxicity | 0.6 |
| 10 | 90 | 0 | 3.4 |
| 3.2 | 5 | 0 | 4.7 |
| 1.0 | 0 | 0 | 4.9 |
| 0.32 | 0 | 0 | 5.2 |
| 0 (Virus Control) |  |  | 5.5 |
| DHPG |  |  |  |
| 320 μg/ml | 100 | sl. toxicity | 0 |
| 100 | 100 | 0 | 0 |
| 32 | 100 | 0 | 0 |
| 10 | 95 | 0 | 1.0 |
| 3.2 | 60 | 0 | 2.3 |
| 1.0 | 30 |  | 3.6 |
| 0.32 | 5 |  | 4.6 |
| 0.1 | 0 |  | 4.7 |
| 0 (virus Control) |  |  | 5.3 |

$^1$Cytopathsgenic Effects = microscopically visible morphological changes in host cells.
$^1$Cell Culture Inhibitory Dose to achieve 50% inhibition.

| Antiviral Compound | MIC50* (mg/ml) |
|---|---|
| ±2'-CdG | 0.11 |
| ±C-2,6'-DAPdR | 0.05 |
| Ara-A | 1.33 |
| DHPG | 0.07 |

*Median Inhibitory Concentration required to achieve 50% inhibition of virus replication.

TABLE 2

Effect of Combination Treatment[a] With (±)-2'-CDG and DHPG on HCMV Replication in MRC5 Cells (Virus Yield-Reduction Assay)

| (±)-2'-CDG Concentration | Reduction in CMV Yield ($\log_{10}$ PFU/ML)[b] DHPG Concentration (μM) | | | |
|---|---|---|---|---|
| (mM) | 0 | 1.0 | 3.2 | 10.0 |
| 0 | 0 | 0.5 | 1.3 | 1.8 |
| 0.1 | 0.1. | 0.5 | 1.3 | 1.9 |
| 0.32 | 0.5 | 0.7 | 1.1 | 2.1 |
| 1.0 | 0.6 | 0.7 | 1.7 | 2.1 |
| 3.2 | 1.0 | 1.2 | 2.0 | 2.7 |

The following results were obtained in testing mixtures of racemic 2'-CdG and papaverine under the same conditions:

TABLE 3

Effect of Combination Treatment[a] With Papaverine and (±)-2'-CDG and on HCMV Replication in MRC5 Cells (Virus Yield-Reduction Assay)

| (±)-2'-CDG Concentration | Reduction in CMV Yield ($\log_{10}$ PFU/ML)[b] DHPG Concentration (μM) | | | | |
|---|---|---|---|---|---|
| (mM) | 0 | 1.0 | 3.2 | 10.0 | 32.0 |
| 0 | 0 | 0 | 0.2 | 0.6 | 1.4 |
| 0.32 | 0.7 | 1.1 | 1.7 | 2.7 | 4.9 |
| 1.0 | 1.0 | 2.0 | 2.1 | 3.9 | 4.6 |
| 3.2 | 1.7 | 2.2 | 3.1 | 4.3 | 5.2 |
| 10.0 | 2.7 | 2.9 | 3.8 | 4.6 | 4.6 |

[a]Drug treatment began immediately following the virus adsorption period (1 ½ hr).
[b]PFU = plaque forming units

Example 2

The D- and L-enantiomers of 2'-CdG were prepared from racemic C-2,6-DAPdR by an enzymatic method as described by Secrist et al, *J. Med- Chem.* Vol. 30, 746–9 (1987). The racemic C-2,6-DAPdR was subjected to the action of commercially available adenosine deaminase 0.5 Unit/μ mole in phosphate buffer (pH 7.4) for 1.5–2 hr at 25° C.±2° C., the solution then was boiled to inactivate the enzyme, and concentrated, after which D-2'-CdG crystallized from solution; yield 70–80% (based on the theoretical yield from one-half of the racemic C-2,6-DAPdR). The remaining unconverted C-2,6-DAPdR was isolated from the filtrate and converted to L-2'-CdG similarly by increasing the concentration of adenosine deaminase to 4 Units/μmole, raising the temperature to 37° C., and lengthening the reaction time to 3 days.

The effectiveness of racemic 2'-CdG and of D-2'-CdG on CMV yields in MRC5 cell monolayer cultures was determined by a plaque assay with the results set forth in Tables 4 and 5:

TABLE 4

The Effect of the Carbocyclic Analogue of (±)-2'-CDG and Deoxyguanosine (±)-2'-CDG on CMV Yields in MRC5 Cells Cell Monolayer Cultures

| (±)-2'-CDG[a] | Reduction (%) of CPE by CDG at Time of Harvest | CMV Yield ($\log_{10}$ CCID$_{50}$/mL) | Drug Cytotoxicity (Gross Morphology) |
|---|---|---|---|
| 32 (μg/mL) | — | — | toxic |
| 10 | 100 | 0 | sl. toxicity |
| 3.2 | 100 | 1.0 | v. sl. |
| 1.0 | 95 | 3.6 | 0 |
| 0.32 | 20 | 4.5 | 0 |
| 0.1 | 0 | 5.0 | 0 |
| 0.032 | 0 | 5.4 | 0 |
| 0 (Virus Control) | — | 5.5 | — |

[a]Drug treatment began immediately following the virus adsorption period (1 ½ hr).

TABLE 5

The Effect of the Carbocyclic Analogue of D-2'-Deoxyguanosine D-2'-CDG on CMV Yields in MRC5 Cells Cell Monolayer Cultures

| D-CDG[a] | Reduction (%) of CPE by D-2'-CDG at Time of Virus Harvest | CMV Yield ($\log_{10}$) PFU/mL | PFU/mL | Drug Cytotoxicity (Gross Morphology) |
|---|---|---|---|---|
| 320 (μM) | — | — | — | toxic |
| 100 | 50 | 0 | | slight toxicity |
| 32 | 50 | 0 | | v. sl. toxicity |
| 10 | 25 | $2 \times 10^1$ | 1.3 | 0 |
| 3.2 | 10 | $8.4 \times 10^2$ | 2.9 | 0 |
| 1.0 | 10 | $5.4 \times 10^3$ | 3.7 | 0 |
| 0.32 | 0 | $1.4 \times 10^4$ | 4.1 | 0 |
| 0.1 | 0 | $3.8 \times 10^4$ | 4.6 | 0 |
| 0 (Virus Controls) | — | $1.1 \times 10^5$ | 5.1 | — |

[a]Drug treatment began immediately following the 1 ½ hour adsorption period.

The MIC$_{50}$ of D-2'-CdG (<0.029 μg/mL) was about half (or less) of the MIC$_{50}$ of DL-2'-CdG (0.069 μg/mL) measured under the same conditions in MRC5 cells. The ED$_{50}$ value (median dose at which 50% antiviral efficacy against CMV is produced) was 0.06 μg/mL for D-2'-CdG and 0.20 for DHPG in human foreskin fibroblast cells.

Example 3

New Zealand white rabbits were found to develop reproducible clinical symptoms of infection within 3–4 days after intravitreal inoculation with human CMV. The symptoms included vitritis, iritis, retinal pathology (micro hemorrhages and focal necrosis of the retinal
"Drug treatment began immediately following the 1½ hour adsorption period.
surface), corneal stromal haze and neovascularization, and corneal endothelial pigmented precipitates. Administration of D-2'-CdG by intravitreal injection i.e., by injection directly within the vitreous humor (100 μg in 100 μl of sterile water) at 48-hour intervals beginning at day 4 was effective in reducing the development of retinal pathology and in reducing the severity of the vitritis and iritis as compared to rabbits receiving a placebo. It was found that in most cases treatment with D-2'-CdG was clinically better than treatment with ganciclovir (DHPG) under the same conditions. The intravitreal route offers some significant advantages for intraocular infections including: 1) delivery of maximal concentrations of drug to the desired site of action; 2) increased potential for sustained release (i.e. longer half-life, $T_{1/2}$) of the drug; and 3) reduced potential for systemic toxicity.

Example 4

Animal models for human CMV disease were prepared by inoculating human CMV by intravitreal injection into pigmented rabbits. The animals developed in 3–4 days post inoculation a mild to moderate vitritis, focal retinal microhemorrhages, and localized retinal necrosis.

Dosages of 2'-CdG of various amounts in 100 μl of sterile water were injected into rabbit models beginning on day 3 post inoculation and repeated on day 5 and day 7N. It was found that a minimal dosage of 40 μg per 100 μl injection was moderately effective in controlling the development of disease. The course of disease development was altered with only a mild vitritis (2+) and focal retinal hemorrhages. Retinal necrosis was evident in all animals at sacrifice.

Dosages of 80 μl of 2'-CdG were effective in reducing the development of vitritis (1–2+ maximum development) and in altering the observed development of retinal pathology. Retinal blood vessel engorgement was evident and focal microhemorrhages were present on days 3, 4, and 5 post inoculation. The development of moderate to severe retinal necrosis and detachment (as observed in the lower concentration 2'CdG therapies and in the placebo treated controls) was not observed. Development and resolution of HCMV intraocular disease in the 80 μg therapy group was similar to disease development in the 100 μg therapy group as described below.

Seven pigmented rabbits were infected with human CMV by intravitreal injection. Beginning on day 3 PI, these animals received 3 successive injections of 100 μg 2'CdG in 50 μl on day 3, 4, and 5 PI. Preliminary results indicate that this daily 2'CdG therapy regimen was effective in reducing the development of human CMV-induced vitritis and retinal pathology. Vitritis scores in these animals were 1–2+ (mild) and retinal pathology was reduced to 1–2+ level (focal hemmorhages and development of localized retinal necrosis). By day 7 post inoculation, these animals had not developed the progressive disease that is observed in the placebo group and the group receiving 2'CdG at two day intervals. Initial virus recovery assays indicate that human CMV titers were reduced to 0 or 1 log by day 2 post therapy.

As is apparent from the foregoing test results, the compounds of the present invention display a high potency in the treatment of fulminant CMV infections.

What is claimed is:

1. A method for preventing or treating cytomegalovirus infections in humans characterized by administering to said human an antiviral effective amount of a compound of the formula

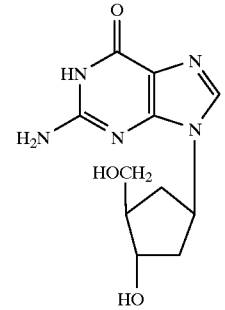

* * * * *